(12) United States Patent
Pierce (nee Fletcher) et al.

(10) Patent No.: US 8,492,398 B2
(45) Date of Patent: Jul. 23, 2013

(54) SPIROAZAINDOLES

(75) Inventors: Joan M. Pierce (nee Fletcher), LaJolla, CA (US); Jeffrey J. Hale, Westfield, NJ (US); Shouwu Miao, Edison, NJ (US); Petr Vachal, Summit, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 159 days.

(21) Appl. No.: 12/991,278

(22) PCT Filed: Apr. 28, 2009

(86) PCT No.: PCT/US2009/041865
§ 371 (c)(1),
(2), (4) Date: Nov. 5, 2010

(87) PCT Pub. No.: WO2009/137291
PCT Pub. Date: Nov. 12, 2009

(65) Prior Publication Data
US 2011/0152304 A1     Jun. 23, 2011

Related U.S. Application Data

(60) Provisional application No. 61/126,895, filed on May 8, 2008.

(51) Int. Cl.
*A61K 31/438* (2006.01)
*C07D 401/14* (2006.01)

(52) U.S. Cl.
USPC .......................................... 514/278; 546/18

(58) Field of Classification Search
USPC .......................................... 514/278; 546/18
See application file for complete search history.

(56) References Cited

U.S. PATENT DOCUMENTS 5,633,247 A    5/1997  Baldwin et al.
2008/0004309 A1  1/2008  Deng et al.

FOREIGN PATENT DOCUMENTS
WO    WO2008/046065 A1    4/2008

OTHER PUBLICATIONS

Mayo Clinic, accessed Aug. 21, 2012, URL: http://www.mayoclinic.com/health/anemia/DS00321/METHOD=print&DSECTION=all.*
McDonough, et al., "Cellular oxygen sensing: Crystal structure of hypoxia-inducible factor prolyl hydroxylase (PHD2)", PNAS, Jun. 2006, vol. 103, No. 26, pp. 9814-9819.

* cited by examiner

*Primary Examiner* — Samantha Shterengarts
(74) *Attorney, Agent, or Firm* — Matthew A. Leff; Patricia A. Shatynski

(57) ABSTRACT

The present invention relates to spiroazaindole compounds useful as HIF prolyl hydroxylase inhibitors to treat anemia and like conditions.

15 Claims, No Drawings

SEQUENCE LISTING

<160> NUMBER OF SEQ ID NOS: 1

<210> SEQ ID NO 1
<211> LENGTH: 19
<212> TYPE: PRT
<213> ORGANISM: Artificial Sequence
<220> FEATURE:
<223> OTHER INFORMATION: PHD2 substrate

```
<400> SEQUENCE: 1

Asp Leu Asp Leu Glu Met Leu Ala Pro Tyr Ile Pro Met Asp Asp Asp
 1               5                  10                  15

Phe Gln Leu
```

SPIROAZAINDOLES

CROSS REFERENCE TO RELATED APPLICATIONS

This application is a U.S. National Phase application under 35 U.S.C. §371 of PCT Application No. PCT/US2009/041865, filed Apr. 28, 2009, which claims priority under 35 U.S.C. §119(e) from U.S. Provisional Application Ser. Nos. 61/126,895, filed May 8, 2008.

BACKGROUND OF THE INVENTION

The insufficient delivery of oxygen to cells and tissues is associated with anemia, which is defined as a deficiency in the blood's oxygen-carrying capacity, and ischemia, in which restrictions in blood supply are caused by a constriction or blockage of blood vessels. Anemia can be caused by the loss of red blood cells (hemorrhage), excessive red blood cell destruction (hemolysis) or deficiencies in erythropoiesis (production of red blood cells from precursors found in the bone marrow). The symptoms of anemia can include weakness, dizziness, fatigue, pallor, impairment of cognitive function and a general reduction in quality of life. Chronic and/or severe anemia can lead to the exacerbation of myocardial, cerebral or peripheral ischemia and to heart failure. Ischemia is defined as an absolute or relative shortage of oxygen to a tissue or organ and can result from disorders such as atherosclerosis, diabetes, thromboembolisms, hypotension, etc. The heart, brain and kidney are especially sensitive to ischemic stress caused by low blood supply.

The primary pharmacological treatment for anemia is administration of some variant of recombinant human erythropoietin (EPO). For anemias associated with kidney disease, chemotherapy-induced anemia, anemia from HIV-therapy or anemia due to blood loss, recombinant EPO is administered to enhance the supply of the hormone, correct the shortage of red blood cells and increase the blood's oxygen-carrying capacity. EPO replacement is not always sufficient to stimulate optimal erythropoiesis (e.g., in patients with iron processing deficiencies) and has associated risks.

Hypoxia-inducible factor (HIF) has been identified as a primary regulator of the cellular response to low oxygen. HIF is a heterodimeric gene transcription factor consisting of a highly regulated α-subunit (HIF-α) and a constitutively expressed β-subunit (HIF-β, also known as ARNT, or aryl hydrocarbon receptor nuclear transporter). HIF target genes are reported to be associated with various aspects of erythropoiesis (e.g., erythropoietin (EPO) and EPO receptor), glycolysis and angiogenesis (e.g., vascular endothelial growth factor (VEGF)). Genes for proteins involved in iron absorption, transport and utilization as well as heme synthesis are also targets of HIF.

Under normal oxygenation, HIF-α is a substrate in a reaction with molecular oxygen, which is catalyzed by a family of iron(II)-, 2-ketoglutarate- and ascorbate-dependent dioxygenase enzymes called PHD-1 (EGLN2, or egg laying abnormal 9 homolog 2, PHD2 (EGLN1), and PHD3 (EGLN3). Proline residues of HIF-α are hydroxylated (e.g., Pro-402 and Pro-564 of HIF-1α) and the resulting product is a target of the tumor suppressor protein von-Hippel Lindau, a component of an E3 ubiquitin ligase multiprotein complex involved in protein ubiquitination. Under low oxygenation, the HIF-α hydroxylation reaction is less efficient and HIF-α is available to dimerize with HIF-β HIF dimers are translocated to the cell nucleus where they bind to a hypoxia-responsive enhancer element of HIF target genes.

Cellular levels of HIF are known to increase under conditions of hypoxia and after exposure to hypoxia mimetic agents. The latter includes, but is not limited to, specific metal ions (e.g., cobalt, nickel, manganese), iron chelators (e.g., desferrioxamine) and analogs of 2-ketoglurate (e.g., N-oxalyl glycine). The compounds of the present invention inhibit the HIF prolyl hydroxylases (PHD-1, PHD-2, PHD-3) and can also serve to modulate HIF levels. These compounds therefore have utility for the treatment and/or prevention of disorders or conditions where HIF modulation is desirable, such as anemia and ischemia. As an alternative to recombinant erythropoietin therapy, the compounds of the present invention provide a simpler and broader method for the management of anemia.

SUMMARY OF THE INVENTION

The present invention concerns compounds which inhibit HIF prolyl hydroxylase, their use for enhancing endogenous production of erythropoietin, and for treating conditions associated with reduced endogenous production of erythropoietin such as anemia and like conditions, as well as pharmaceutical compositions comprising such a compound and a pharmaceutical carrier.

DETAILED DESCRIPTION OF THE INVENTION

The present invention provides compounds of formula I and pharmaceutically acceptable salts and solvates thereof:

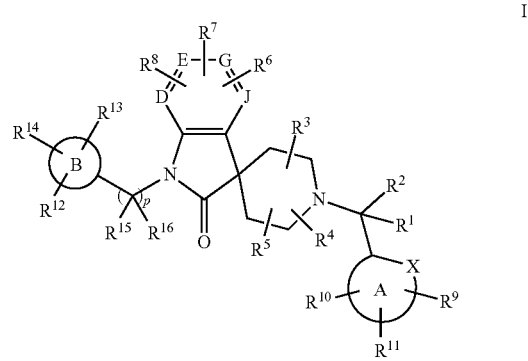

wherein
A is a heterocyle having at least one heteroatom, X, or hydrogen;
X is selected from N, O and S;
B is a carbocycle or a heterocycle;
At least one of D, E, G, and J, is nitrogen;
p is 0 or 1;
$R^1$, $R^2$, $R^{15}$ and $R^{16}$ are independently selected from i) hydrogen; ii) $C_1$-$C_4$ alkyl, optionally substituted with a hydroxy, —SH, —$NH_2$ or —$CO_2H$; iii) trifluoromethyl; iv) 2,2,2-trifluoroethyl; and v) —$CO_2H$;
$R^3$, $R^4$ and $R^5$ are independently selected from hydrogen, F, OH, $C_1$-$C_4$ alkyl, $C_1$-$C_4$ haloalkyl, —$OC_1$-$C_4$ alkyl,)-, ($C_0$-$C_6$ alkyl)$_2$NC(O)—, —($C_0$-$C_6$ alkyl)C(O)NH($C_0$-$C_6$ alkyl), —($C_0$-$C_6$ alkyl)C(O)O($C_0$-$C_6$ alkyl), —($C_0$-$C_6$ alkyl)aryl, —($C_0$-$C_6$ alkyl)C(O)aryl, —($C_0$-$C_6$ alkyl)C(O)heteroaryl, and —($C_0$-$C_6$ alkyl)heteroaryl, where aryl, heteroaryl and are each optionally substituted with one to three groups independently selected from halo, $C_1$-$C_6$ alkyl, —O($C_1$-$C_6$ alkyl) and cyano;

R³ and R⁴ attached to the same carbon atom together form an oxo group or complete a $C_3$-$C_6$ cycloalkyl ring, or R³ and R⁴ attached to adjacent carbon atoms together complete a $C_3$-$C_6$ cycloalkyl ring, or R³ and R⁴ attached to nonadjacent carbon atoms together represent $C_1$-$C_2$ alkylene;

$R^6$, $R^7$, $R^8$, $R^9$, $R^{10}$, $R^{11}$, $R^{12}$, $R^{13}$ and $R^{14}$ are independently selected from hydrogen, halo, $C_1$-$C_6$ alkyl optionally substituted with one to five fluorine, $NH_2$, $N(C_1$-$C_6$ alkyl)$_2$, $NO_2$, CN, $N_3$, —OH, —O($C_1$-$C_6$ alkyl) optionally substituted with one to five fluorine, $C_3$-$C_{10}$ cycloalkyl, $C_2$-$C_6$ alkenyl, $C_2$-$C_6$ alkynyl, —O-aryl, aryl-S(O)$_{0-2}$—, ($C_0$-$C_6$ alkyl)S(O)$_{0-2}$($C_0$-$C_6$ alkylene)-, ($C_0$-$C_6$ alkyl)C(O)NH—, $H_2N$—C(NH)—, ($C_0$-$C_6$ alkyl)C(O)—, ($C_0$-$C_6$ alkyl)OC(O)($C_0$-$C_6$ alkylene)-, ($C_0$-$C_6$ alkyl)O($C_1$-$C_6$ alkylene)-, ($C_0$-$C_6$ alkyl)C(O)$_{1-2}$($C_0$-$C_6$ alkylene)-, ($C_0$-$C_6$ alkyl)$_2$NC(O)—, ($C_0$-$C_6$ alkyl)OC(O)NH—, aryl, aralkyl, heteroaryl, and heteroaralkyl, where aryl, aralkyl, heteroaryl and heteroaralkyl are each optionally substituted with one to three groups, $R^{17}$, $R^{18}$ and $R^{19}$, independently selected from halo, $C_1$-$C_6$ alkyl, —O($C_1$-$C_6$ alkyl) and cyano;

wherein any two of $R^{12}$, $R^{13}$, $R^{14}$, $R^{17}$, $R^{18}$ and $R^{19}$ together with the atoms of the ring system, B, form a 5 to 8-membered ring.

In one subset of formula I are compounds wherein A is a 5-membered heteroaromatic ring in which X is nitrogen, and the ring optionally having one to three additional heteroatoms selected from N, O and S. In one embodiment in this subset, A is imidazol-2-yl. In a second embodiment A is 2-pyrroyl.

In a second subset of formula I are compounds wherein A is a 6-membered heteroaromatic ring in which X is nitrogen, and the ring optionally having one additional nitrogen atom. In one embodiment in this subset A is 2-pyridyl.

In a third subset of formula I are compounds wherein the group

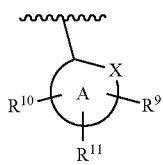

is selected from hydrogen, 1-methyl-2-imidazolyl, 3-methyl-2-pyridyl, 3-cyclopropyl-2-pyridyl, 1-(2-pyridylmethyl)-2-pyrrolyl, 1-(methoxycarbonylmethyl)-2-imidazolyl, 1-(carboxymethyl)-2-imidazolyl, 3,5-dimethyl-2-pyridyl, 1-benzyl-2-imidazolyl, 3-trifluoromethyl-2-pyridyl, 3-(methoxy carbonyl)methyl-2-pyridyl, 1-(aminocarbonyl methyl)-2-imidazolyl, 1-(aminocarbonyl methyl)-2-pyridinyl, 3-carboxy-2-pyridyl, 1-(aminocarbonyl)-2-pyridinyl, 1-(aminocarbonyl)-2-imidazolyl imidazolyl, carboxyl, and 1-(carboxyethyl)-1-imidazolyl.

In a variant of the third subset of formula I are compounds wherein the group

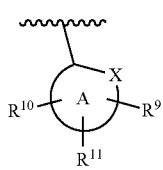

is selected from 3-methyl-2-pyridyl, —CO$_2$H.

In a fourth subset of formula I are compounds wherein B is aryl. In one embodiment B is phenyl. In another embodiment, B is naphthyl. In yet another embodiment B is biphenyl.

In a fifth subset of formula I are compounds wherein B is a 7- to 12-membered bicyclic heterocycle. In one embodiment B is an 8- to 12-membered bicyclic heteroaromatic ring system; in one subgroup B is an 8- to 10-membered fused bicyclic heteroaromatic ring system, and in another subgroup B is a 10- to 12-membered bicyclic heteroaromatic ring system wherein each ring is attached to the other via a bond. In another embodiment B is a 7- to 12-membered bicyclic unsaturated heterocycle.

In a sixth subset of formula I are compounds wherein B is selected from the group consisting of phenyl, 4-biphenyl, 3-biphenyl, 1-naphthyl, 2-naphthyl, 3-quinolinyl, 5-quinolinyl, 6-quinolinyl, 7-quinolinyl, 6-isoquinolinyl, 7-quinoxalinyl, 6-quinazolinyl, 7-cinnolinyl, 5-indolyl, pyrazolo[3,4-b]pyrid-5-yl, 1,4-benzoxazinyl, 1,3-benzoxazolinyl, pyrrolyl)phenyl, 4-(3-pyridyl)phenyl, 641-pyrrolyl)-3-pyridyl, pyridyl, chromonyl, thiazolyl, thienyl, 4-(2-thienyl)-phenyl, fluorenyl, (9-oxo)-2-fluorenyl, 2-phenyl)-4-(1,3-thiazolyl), and 2-phenyl-5-(1,3-thiazolyl).

In a seventh subset of formula I are compounds wherein the group B is biphenyl.

In one embodiment of the invention, $R^6$, $R^7$, $R^8$ are each independently chosen from hydrogen, halo, $C_1$-$C_6$ alkyl optionally substituted with one to five fluorine, —CO$_2$H and —CN.

In an other embodiment of the invention, $R^3$, $R^4$, $R^5$ are each independently chosen from hydrogen, carboxyl, acetic acid, —C(OH)CO$_2$H, pyridinyl carbonyl-, —C(OH)pyridinyl, —C(OH)CO$_2$C$_{1-6}$alkyl, —C(OH)CONH$_2$, —C(OH)CONHC(CH$_3$)$_2$, and —C(OH)CONHCH$_2$CO$_2$H. In a variant of this embodiment, $R^3$, $R^4$, $R^5$ are each independently chosen from hydrogen and $C_{1-6}$alkyl optionally substituted with one or more halo, hydroxyl, —CN and —NH$_2$.

In an eighth subset of formula I are compounds wherein p is 0.

In a ninth subset of formula I are compounds wherein A and $R^1$ are both hydrogen, and $R^2$ is —CO$_2$H.

In one embodiment of the invention, D is nitrogen.

In another embodiment of the invention, E is nitrogen.

In yet another embodiment of the invention, G is nitrogen.

In still yet another embodiment of the invention, J is nitrogen.

Non-limiting examples of the compounds of the present invention include:

Non-limiting examples of the compounds of the present invention include:

1'-biphenyl-4-yl-1-[(3-methylpyridin-2-yl)methyl]spiro[piperidine-4,3'-pyrrolo[3,2-b]pyridin]-2'(1'H)-one;

1'-biphenyl-4-yl-1-[(3-methylpyridin-2-yl)methyl]spiro[piperidine-4,3'-pyrrolo[2,3-b]pyridin]-2'(1'H)-one;

1'-biphenyl-4-yl-1-[(3-methylpyridin-2-yl)methyl]-2'-oxo-1',2'-dihydrospiro[piperidine-4,3'-pyrrolo[2,3-b]pyridine]-6'-carbonitrile;

1'-biphenyl-4-yl-1-[(3-methylpyridin-2-yl)methyl]-2'-oxo-1',2'-dihydrospiro[piperidine-4,3'-pyrrolo[2,3-b]pyridine]-5'-carbonitrile 1'-biphenyl-4-yl-1-[(3-methylpyridin-2-yl)methyl]-2'-oxo-1',2'-dihydrospiro[piperidine-4,3'-pyrrolo[2,3-b]pyridine]-5'-carboxylic acid;

1'-biphenyl-4-yl-1-[(3-methylpyridin-2-yl)methyl]-2'-oxo-1',2'-dihydrospiro[piperidine-4,3'-pyrrolo[2,3-b]pyridine]-6'-carboxylic acid;

(1'-biphenyl-4-yl-5'-bromo-2'-oxo-1',2'-dihydro-1H-spiro[piperidine-4,3'-pyrrolo[2,3-b]pyridin]-1-yl)acetic acid;

(1'-biphenyl-4-yl-5'-cyano-2'-oxo-1',2'-dihydro-1H-spiro [piperidine-4,3'-pyrrolo[2,3-b]pyridin]-1-yl)acetic acid;
(1'-biphenyl-4-yl-2'-oxo-1',2'-dihydro-1H-spiro[piperidine-4,3'-pyrrolo[2,3-b]pyridin]-1-yl)acetic acid;
1'-biphenyl-4-yl-1-(carboxymethyl)-2'-oxo-1',2'-dihydrospiro[piperidine-4,3'-pyrrolo[2,3-b]pyridine]-5'-carboxylic acid and pharmaceutically acceptable salts and solvates thereof.

As used herein, unless specified otherwise, "alkyl" includes both branched- and straight-chain saturated aliphatic hydrocarbon groups, including all isomers, having the specified number of carbon atoms; for example, "$C_{1-6}$ alkyl" (or "$C_1$-$C_6$ alkyl") includes all of the hexyl alkyl and pentyl alkyl isomers as well as n-, iso-, sec- and t-butyl, n- and isopropyl, ethyl and methyl. "Alkylene" refers to both branched- and straight-chain saturated aliphatic hydrocarbon groups, including all isomers, having the specified number of carbons, and having two terminal end chain attachments; for example, the term "A-$C_4$alkylene-B" represents, for example, A-$CH_2$—$CH_2$—$CH_2$—$CH_2$—B, A-$CH_2$—$CH_2$—CH($CH_3$)—$CH_2$—B, A-$CH_2$—CH($CH_2CH_3$)—B, A-$CH_2$—C($CH_3$)($CH_3$)—B, and the like. "Alkoxy" represents a linear or branched alkyl group of indicated number of carbon atoms attached through an oxygen bridge; for example "$C_1$-$C_6$ alkoxy" includes —$OCH_3$, —$OCH_2CH_3$, —$OCH(CH_3)_2$, —$O(CH_2)_5CH_3$, and the like.

Unless otherwise specifically noted as only "unsubstituted" or only "substituted", alkyl groups are unsubstituted or substituted with 1 to 3 substituents on each carbon atom, with halo, $C_1$-$C_{20}$ alkyl, $CF_3$, $NH_2$, N($C_1$-$C_6$ alkyl)$_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_0$-$C_6$ alkyl) S(O)$_{0-2}$—, ($C_0$-$C_6$ alkyl)S(O)$_{0-2}$($C_0$-$C_6$ alkyl)-, ($C_0$-$C_6$ alkyl)C(O)NH—, $H_2N$—C(NH)—, —O($C_1$-$C_6$ alkyl)$CF_3$, ($C_0$-$C_6$ alkyl)C(O)—, ($C_0$-$C_6$ alkyl)OC(O)—, ($C_0$-$C_6$ alkyl)O($C_1$-$C_6$ alkyl)-, ($C_0$-$C_6$ alkyl)C(O)$_{1-2}$($C_0$-$C_6$ alkyl)-, ($C_0$-$C_6$ alkyl)OC(O)NH—, —NH($C_1$-$C_6$ alkyl)NHC(O)NH($C_1$-$C_6$ alkyl), NHC(O)O$C_1$-$C_6$ alkyl, —NH($C_1$-$C_6$ alkyl)NHSO$_2$($C_1$-$C_6$ alkyl), —($C_0$-$C_6$ alkyl)NHSO$_2$($C_1$-$C_6$ alkyl), aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl.

The term "alkenyl" means a straight or branched carbon chain having the specified number of carbon atoms with at least one carbon-carbon double bond. Examples of alkenyl include, but are not limited to, vinyl, allyl, isopropenyl, pentenyl, hexenyl, heptenyl, 1-propenyl, 2-butenyl, 2-methyl-2-butenyl, 2,4-hexadienyl, and the like.

The term "alkynyl" means a straight or branched carbon chain having the specified number of carbon atoms with at least one carbon-carbon triple bond. Examples of alkynyl include, but are not limited to ethynyl, propargyl, 1-propynyl, 2-butynyl, and the like.

The term "carbocycle" (and variations thereof such as "carbocyclic" or "carbocyclyl") as used herein, unless otherwise indicated, refers to (i) a $C_3$ to $C_8$ monocyclic, saturated or unsaturated ring or (ii) a $C_7$ to $C_{12}$ bicyclic saturated or unsaturated ring system. Each ring in (ii) is either attached via a bond to, or fused (including spirofused) to, the other ring, and each ring is saturated or unsaturated. The carbocycle may be attached to the rest of the molecule at any carbon atom which results in a stable compound.

Saturated carbocyclics form a subset of carbocycles in which the entire ring system (mono- or polycyclic) is saturated. Saturated monocyclic carbocyclic rings are also referred to as cycloalkyl rings, e.g., cyclopropyl, cyclobutyl, etc. The fused bicyclic carbocycles are a further subset of the carbocycles in which a $C_7$ to $C_{10}$ bicyclic ring system in which each ring is saturated or unsaturated and two adjacent carbon atoms (or in the case of spirofused, one carbon atom) are shared by each of the rings in the ring system. A saturated bicyclic carbocycle is one in which both rings are saturated. An unsaturated bicyclic carbocycle is one in which one ring is unsaturated and the other is unsaturated or saturated. Unless otherwise noted, carbocycle is unsubstituted or substituted with $C_{1-6}$ alkyl, $C_{1-6}$ alkenyl, $C_{1-6}$ alkynyl, aryl, halogen, $NH_2$ or OH. A subset of the fused bicyclic unsaturated carbocycles are those bicyclic carbocycles in which one ring is a benzene ring and the other ring is saturated or unsaturated, with attachment via any carbon atom that results in a stable compound. Representative examples of this subset include the following:

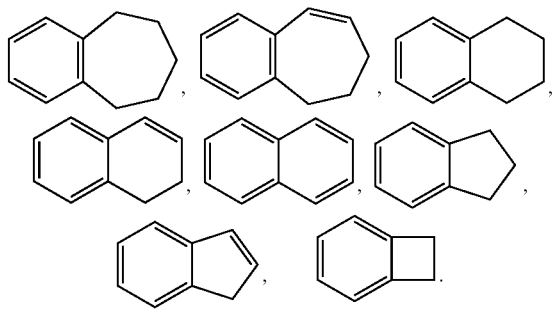

Aromatic carbocycles form another subset of the carbocycles. The term "aryl" refers to aromatic mono- and polycarbocyclic ring systems in which the individual carbocyclic rings in the polyring systems are fused or attached to each other via a single bond. Suitable aryl groups include phenyl, naphthyl, and biphenyl.

The term "cycloalkyl" means a cyclic ring of an alkane having the specified total ring carbon atoms; for example cyclopropyl, cyclobutyl, cyclopentyl, cyclohexyl.

The term "heterocycle" (and variations thereof such as "heterocyclic" or "heterocyclyl") broadly refers to (i) a stable 4- to 8-membered, saturated or unsaturated monocyclic ring, or (ii) a stable 7- to 12-membered bicyclic ring system, wherein each ring in (ii) is either attached via a bond to, or fused (including spirofused) to, the other ring, and each ring is saturated or unsaturated, and the monocyclic ring or bicyclic ring system contains one or more heteroatoms (e.g., from 1 to 6 heteroatoms, or from 1 to 4 heteroatoms) selected from N, O and S and a balance of carbon atoms (the monocyclic ring typically contains at least one carbon atom and the ring systems typically contain at least two carbon atoms); and wherein any one or more of the nitrogen and sulfur heteroatoms is optionally oxidized, and any one or more of the nitrogen heteroatoms is optionally quaternized. Unless otherwise specified, the heterocyclic ring may be attached at any heteroatom or carbon atom, provided that attachment results in the creation of a stable structure. Unless otherwise specified, when the heterocyclic ring has substituents, it is understood that the substituents may be attached to any atom in the ring, whether a heteroatom or a carbon atom, provided that a stable chemical structure results.

Saturated heterocyclics form a subset of the heterocycles; i.e., the term "saturated heterocyclic" generally refers to a heterocycle as defined above in which the entire ring system (whether mono- or poly-cyclic) is saturated. The term "saturated heterocyclic ring" refers to a 4- to 8-membered saturated monocyclic ring or a stable 7- to 12-membered bicyclic ring system which consists of carbon atoms and one or more heteroatoms selected from N, O and S. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, 1,4-dioxanyl, 1,4-thioxanyl, tetrahydropyranyl, tetrahydrofuryl (or tetrahydrofuranyl), tetrahydrothienyl, and tetrahydrothiopyranyl.

Heteroaromatics form another subset of the heterocycles; i.e., the term "heteroaromatic" (alternatively "heteroaryl") generally refers to a heterocycle as defined above in which the entire ring system (whether mono- or poly-cyclic) is an aromatic ring system. The term "heteroaromatic ring" refers a 5- or 6-membered monocyclic aromatic ring or a 7- to 12-membered bicyclic aromatic ring, and which consists of carbon atoms and one or more heteroatoms selected from N, O and S. In the case of substituted heteroaryl rings containing at least one nitrogen atom (e.g., pyridine), such substitutions can be those resulting in N-oxide formation. Representative examples of monocyclic heteroaromatic rings include pyridyl, pyrrolyl, pyrazinyl, pyrimidinyl, pyridazinyl, thienyl (or thiophenyl), thiazolyl, furanyl, imidazolyl, pyrazolyl, triazolyl, tetrazolyl, oxazolyl, isoxazolyl, oxadiazolyl, thiazolyl, isothiazolyl, and thiadiazolyl. Examples of bicyclic heteroaromatic rings include benzotriazolyl, indolyl, benzoxazolyl, benzofuranyl, benzothienyl, benzothiazolyl, benzimidazolyl, isoindolyl, indazolyl, quinoxalinyl, quinazolinyl, cinnolinyl, quinolinyl isoquinolinyl, naphthyridinyl, pyrazolo[3,4-b]pyridine, imidazo[2,1-b](1,3)thiazole,

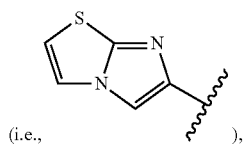 [SMILES: *c1cn2ccsc2n1]

(i.e., ), 6-(1-pyrrolyl)-3-pyridyl, 4-(1-pyrrolyl)phenyl, 4-(pyrid-3-yl)phenyl, and 4-(pyrid-4-yl)phenyl.

Another subset of heterocycles are unsaturated heterocycles in which one or both rings are unsaturated (provided the entire ring system is not aromatic). Representative examples of unsaturated heterocycles include dihydrofuranyl, dihydrothienyl, dihydropyranyl, dihydroimidazolyl, indolinyl, isoindolinyl, chromanyl, isochromanyl, tetrahydroquinolinyl, tetrahydroisoquinolinyl, tetrahydronaphthyridinyl, 2,3-dihydrobenzofuranyl, 1,4-benzoxazinyl, 1,3-benzoxazolinyl, 2,3-dihydrobenzo-1,4-dioxinyl

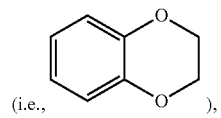

(i.e., ), and benzo-1,3-dioxolyl

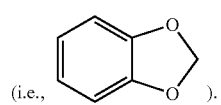

(i.e., ).

In certain contexts herein,

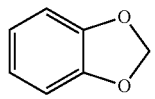

is alternatively referred to as phenyl having as a substituent methylenedioxy attached to two adjacent carbon atoms. Also included are groups such as chromone and coumarin.

Unless otherwise specifically noted as only unsubstituted or only substituted, cycloalkyl, cycloalkenyl, cycloalkyl, aryl (including phenyl) and heteroaryl groups are unsubstituted or substituted (also referred to as "optionally substituted"). Unless the substituents are specifically provided, substituents for substituted or optionally substituted cycloalkyl, cycloalkenyl, aryl (including phenyl, and as an isolated substituent or as part of a substituent such as in aryloxy and aralkyl), heteroaryl (as an isolated substituent or as part of a substituent such as in heteroaryloxy and heteroaralkyl) are one to three groups independently selected from halo, $C_1$-$C_6$ alkyl optionally substituted with one to five fluorine, $NH_2$, $N(C_1$-$C_6$-alkyl)$_2$, $NO_2$, oxo, CN, $N_3$, —OH, —O($C_1$-$C_6$ alkyl) optionally substituted with one to five fluorine, $C_3$-$C_{10}$ cycloalkyl, $C_2$-$C_6$ alkenyl, $C_2$-$C_6$ alkynyl, ($C_0$-$C_6$ alkyl)S(O)$_{0-2}$—, aryl-S(O)$_{0-2}$—, ($C_0$-$C_6$ alkyl)S(O)$_{0-2}$($C_0$-$C_6$ alkylene)-, ($C_0$-$C_6$ alkyl)C(O)NH—, $H_2N$—C(NH)—, ($C_0$-$C_6$ alkyl)C(O)—, ($C_0$-$C_6$ alkyl)OC(O)—, ($C_0$-$C_6$alkyl)O($C_1$-$C_6$ alkylene)-, ($C_0$-$C_6$ alkyl)C(O)$_{1-2}$($C_0$-$C_6$ alkylene)-, ($C_0$-$C_6$ alkyl)$_2$NC(O)—, ($C_0$-$C_6$ alkyl)OC(O)NH—, aryl, aralkyl, heteroaryl, heteroaralkyl, halo-aryl, halo-aralkyl, halo-heteroaryl, halo-heteroaralkyl, cyano-aryl, cyano-aralkyl, cyano-heteroaryl and cyano-heteroaralkyl.

The term "halogen" (or "halo") refers to fluorine, chlorine, bromine and iodine (alternatively referred to as fluoro (F), chloro (Cl), bromo (Br), and iodo (I)).

The term "haloalkyl" means alkyl having the specified number of carbon atoms in which from one to all of the hydrogen atoms have been replaced by a halogen atom.

The terms "aralkyl" and "heteroaralkyl" refer to an aryl/heteroaryl linked to rest of the molecule via a $C_1$ to $C_4$ alkylene.

The term "$C_0$" as employed in expressions such as "$C_{0-6}$ alkylene" means a direct covalent bond; or when employed in expressions such as "$C_{0-6}$ alkyl" means hydrogen.

Similarly, when an integer defining the presence of a certain number of atoms in a group is equal to zero, it means that the atoms adjacent thereto are connected directly by a bond; for example, in the structure

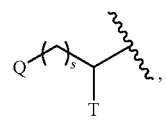

wherein s is an integer equal to zero, 1 or 2, the structure is

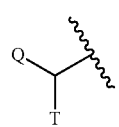

when s is zero; or it means that the indicated atom is absent; for example —S(O)$_0$— means —S—.

Unless expressly stated to the contrary, an "unsaturated" ring is a partially or fully unsaturated ring. For example, an "unsaturated monocyclic C$_6$ carbocycle" refers to cyclohexene, cyclohexadiene, and benzene.

Unless expressly stated to the contrary, all ranges cited herein are inclusive. For example, a heterocycle described as containing from "1 to 4 heteroatoms" means the heterocycle can contain 1, 2, 3 or 4 heteroatoms.

When any variable occurs more than one time in any constituent or in any formula depicting and describing compounds of the invention, its definition on each occurrence is independent of its definition at every other occurrence. Also, combinations of substituents and/or variables are permissible only if such combinations result in stable compounds. For variable definitions containing terms having repeated terms, e.g., (CR$^i$R$^j$)$_r$, where r is the integer 2, R$^i$ is a defined variable, and R$^j$ is a defined variable, the value of R$^i$ may differ in each instance in which it occurs, and the value of R$^j$ may differ in each instance in which it occurs. For example, if R$^i$ and R$^j$ are independently selected from the group consisting of methyl, ethyl, propyl and butyl, then (CR$^i$R$^j$)$_2$ can be

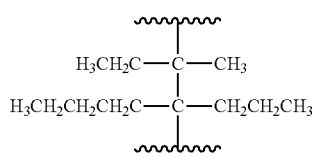

Optical Isomers—Diastereomers—Geometric Isomers—Tautomers

Compounds described herein may contain an asymmetric center and may thus exist as enantiomers. Where the compounds according to the invention possess two or more asymmetric centers, they may additionally exist as diastereomers. The present invention includes all such possible stereoisomers as substantially pure resolved enantiomers, racemic mixtures thereof, as well as mixtures of diastereomers. The above Formula I is shown without a definitive stereochemistry at certain positions. The present invention includes all stereoisomers of Formula I and pharmaceutically acceptable salts thereof. Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of the general Formula I may be obtained by stereospecific synthesis using optically pure starting materials or reagents of known configuration.

When compounds described herein contain olefinic double bonds, unless specified otherwise, such double bonds are meant to include both E and Z geometric isomers.

Some of the compounds described herein may exist with different points of attachment of hydrogen, referred to as tautomers. For example, compounds including carbonyl —CH$_2$C(O)— groups (keto forms) may undergo tautomerism to form hydroxyl-CH=C(OH)— groups (enol forms). Both keto and enol forms, individually as well as mixtures thereof, are included within the scope of the present invention.

Salts

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Preferred are the ammonium, calcium, magnesium, potassium and sodium salts. Salts prepared from pharmaceutically acceptable organic non-toxic bases include salts of primary, secondary, and tertiary amines derived from both naturally occurring and synthetic sources. Pharmaceutically acceptable organic non-toxic bases from which salts can be formed include, for example, arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, dicyclohexylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

Solvates

The present invention includes within its scope solvates of compounds of Formula I. As used herein, the term "solvate" refers to a complex of variable stoichiometry formed by a solute (i.e., a compound of Formula I) or a pharmaceutically acceptable salt thereof and a solvent that does not interfere with the biological activity of the solute. Examples of solvents include, but are not limited to water, ethanol, and acetic acid. When the solvent is water, the solvate is known as hydrate; hydrate includes, but is not limited to, hemi-, mono, sesqui-, di- and trihydrates.

Prodrugs

The present invention includes within its scope the use prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with a compound of formula I or with a compound which may not be a compound of formula I, but which converts to a compound of formula I in vivo after administration to the patient. Conventional procedures for the selection and preparation of suitable prodrug derivatives are described, for example, in "Design of Prodrugs," ed. H. Bundgaard, Elsevier, 1985.

Utilities

Compounds of the present invention are inhibitors of hypoxia-inducible factor (HIF) prolyl hydroxylases, and as such are useful in the treatment and prevention of diseases and conditions in which HIF modulation is desirable, such as anemia and ischemia. Compounds of the invention can be used in a selective and controlled manner to induce hypoxia-inducible factor stabilization and to rapidly and reversibly stimulate erythropoietin production and secretion. Accordingly, another aspect of the present invention provides a method of treating or preventing a disease or condition in a mammal, the treatment or prevention of which is effected or facilitated by HIF prolyl hydroxylase inhibition, which comprises administering an amount of a compound of Formula I that is effective for inhibiting HIF prolyl hydroxylase. This aspect of the present invention further includes the use of a compound of Formula I in the manufacture of a medicament for the treatment or prevention of a disease or condition modulated by HIF prolyl hydroxylase.

In one embodiment is a method of enhancing endogenous production of erythropoietin in a mammal which comprises administering to said mammal an amount of a compound of Formula I that is effective for enhancing endogenous production of erythropoietin.

Another embodiment is a method of treating anemia in a mammal which comprises administering to said mammal a therapeutically effective amount of a compound of Formula I. "Anemia" includes, but is not limited to, chronic kidney disease anemia, chemotherapy-induced anemia (e.g., anemia resulting from antiviral drug regimens for infectious diseases, such as HIV and hepatitis C virus), anemia of chronic disease, anemia associated with cancer conditions, anemia resulting from radiation treatment for cancer, anemias of chronic immune disorders such as rheumatoid arthritis, inflammatory bowel disease, and lupus, and anemias due to menstruation or of senescence or in other individuals with iron processing deficiencies such as those who are iron-replete but unable to utilize iron properly.

Another embodiment is a method of treating ischemic diseases in a mammal, which comprises administering to said mammal a therapeutically effective amount of a compound of Formula I.

Combination Therapy

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I.

Route of Administration/Dosage

The compounds of this invention can be administered for the treatment or prevention of afflictions, diseases and illnesses according to the invention by any means that effects contact of the active ingredient compound with the site of action in the body of a warm-blooded animal. For example, administration can be oral, topical, including transdennal, ocular, buccal, intranasal, inhalation, intravaginal, rectal, intracisternal and parenteral. The term "parenteral" as used herein refers to modes of administration which include subcutaneous, intravenous, intramuscular, intraarticular injection or infusion, intrasternal and intraperitoneal. For the purpose of this disclosure, a warm-blooded animal is a member of the animal kingdom possessed of a homeostatic mechanism and includes mammals and birds.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

The dosage administered will be dependent on the age, health and weight of the recipient, the extent of disease, kind of concurrent treatment, if any, frequency of treatment and the nature of the effect desired. Usually, a daily dosage of active ingredient compound will be from about 1.0-2000 milligrams per day. Ordinarily, from 10 to 500 milligrams per day in one or more applications is effective to obtain desired results. These dosages are the effective amounts for the treatment and prevention of afflictions, diseases and illnesses described above, e.g., anemia.

Pharmaceutical Composition

Another aspect of the present invention provides pharmaceutical compositions which comprises a compound of Formula I and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

The pharmaceutical compositions of the present invention comprise a compound represented by Formula I (or pharmaceutically acceptable salts thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

The active ingredient can be administered orally in solid dosage forms, such as capsules, tablets, troches, dragées, granules and powders, or in liquid dosage forms, such as elixirs, syrups, emulsions, dispersions, and suspensions. The active ingredient can also be administered parenterally, in sterile liquid dosage forms, such as dispersions, suspensions or solutions. Other dosages forms that can also be used to administer the active ingredient as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene gycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences*, A. Osol, a standard reference text in this field.

For administration by inhalation, the compounds of the present invention may be conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula I in suitable propellants, such as fluorocarbons or hydrocarbons.

For ocular administration, an ophthalmic preparation may be formulated with an appropriate weight percent solution or suspension of the compounds of Formula I in an appropriate ophthalmic vehicle, such that the compound is maintained in contact with the ocular surface for a sufficient time period to allow the compound to penetrate the corneal and internal regions of the eye.

Useful pharmaceutical dosage-forms for administration of the compounds of this invention include, but are not limited to, hard and soft gelatin capsules, tablets, parenteral injectables, and oral suspensions.

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

A parenteral composition suitable for administration by injection is prepared by stirring 1.5% by weight of active ingredient in 10% by volume propylene glycol. The solution is made to volume with water for injection and sterilized.

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise or in conjunction with another therapeutic agent. When drugs are administered in physical combination, the dosage form and administration route should be selected depending on the compatibility of the combined drugs. Thus the term coadministration is understood to include the administration of the two agents concomitantly or sequentially, or alternatively as a fixed dose combination of the two active components.

Synthesis

Methods for preparing the compounds of this invention are illustrated in the following schemes. Other synthetic protocols will be readily apparent to those skilled in the art. The examples illustrate the preparation of the compounds of Formula I and as such are not to be considered as limiting the invention set forth in the claims appended hereto. Unless otherwise indicated, all variables are as previously defined.

Abbreviations used herein are as follows: Ac=acetyl; BOC=t-butoxycarbonyl; DCM=dichloromethane; DME=dimethylether; DMF=dimethylformamide; LiHMDS=lithium hexamethyldisilazane; Me=methyl; TFA=trifluoroacetic acid

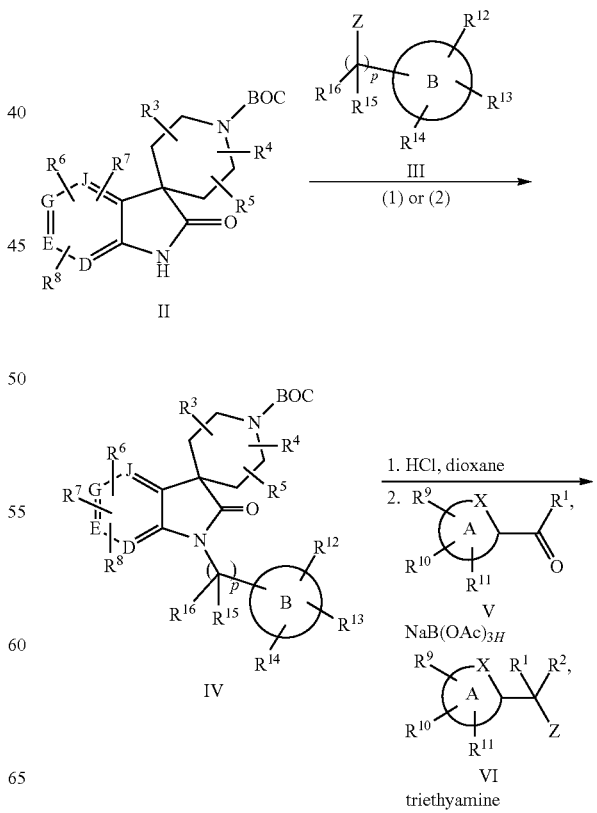

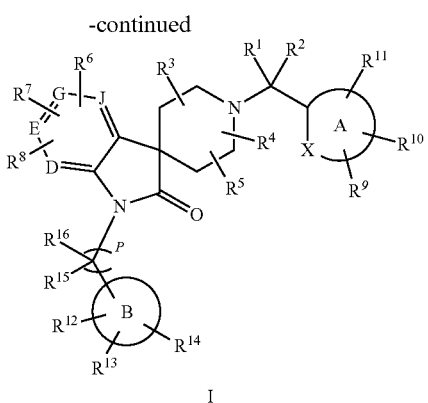

I

Z is halogen
(1) p is 0, and B is aryl or heteroaryl: CuI, K₂CO₃, MeCN, CH₃NH(CH₂)₂NHCH₃
(2) p is 0, and B is other than aryl or heteroaryl, or p is 1 and B is carbocycle or heterocycle: KF-alumina, MeCN Compounds of formula II may be prepared by methods known in the art such as those described in (a) Freund, R.; Mederski, W. K. R. *Helvetica Chimica Acta* 2000, 83, 1247. (b) Ganguly, A. K.; Wang, C. H; David, M.; Bartner, P.; Chan, T. M. *Tetrahedron Lett.* 2002, 43, 6865. (c) Bell, I. M.; Gallicchio, S. N.; Theberge, C. R.; Zhang, X.-F.; Stump, C.; Zartman, C. B., WO2004082605. As illustrated in the above Scheme, a compound of formula II can be converted to a compound of formula IV by reaction with a compound of formula III. In one aspect where B is an aryl or heteroaryl, the reaction is carried out using copper salts (such as CuI), a base (such as anhydrous potassium carbonate) and a diamine ligand (such as N,N'-dimethylethylenediamine or N,N'-dimethyl-1,2-cyclohexanediamine) in organic solvents (such as acetonitrile or dioxane). Alternatively, the conversion of compound II to compound IV, where B is an aryl or heteroaryl, is accomplished by a reaction of II with III, in which Z is boronic acid (Z=—B(OH)2) or boronic acid ester, using a tertiary organic or inorganic base (such as triethylamine, N,N-diisopropylethylamine, and sodium hydride) and copper salts (such as Cu(OAc)2, CuCl2) in various solvents (such as methylene chloride, THF, dioxane, acetonitrile): Konkel, M. J.; Packiarajan, M.; Chen, H.; Topiwala, U. P.; Jimenez, H.; Talisman, I. J.; Coate, H.; Walker, M. W *Bioorg. Med. Chem. Lett.* 2006, 16, 3950-3954. In some cases, conversion of II to IV is accomplished using copper salts (such as cooper bromide), strong base (such as sodium hydride) in various solvents (such as N,N-dimethylformamide).

In second aspect where B is other then an aryl or heteroaryl or p is 1 and B is carbocycle or heterocycle, conversion of II to IV is accomplished by reaction with the respective electrophile III (in which Z is for example a halogen, triflate, mesylate) promoted by KF on alumina in organic solvent (such as acetonitrile). The transformation is alternatively accomplished with a strong base (such as sodium hydride, potassium tert-butoxide) in organic solvents (such as N,N-dimethylformamide).

Deprotection of the Boc-group in IV is accomplished by a reaction with an acid such as hydrogen chloride, trifluoroacetic acid, sulfuric acid, or hydrogen bromide, either neat or in organic solvents such as methylene chloride, dioxane, and ether.

Formation of I is accomplished by a one-pot reductive amination of the product of the Boc-deprotection using carbonyl compound V and a reducing agent (such as sodium triacetoxyborohydride) or by a stepwise procedure analogous to Scheme 1 forming an imine with corresponding carbonyl compound V first, and then subsequently reducing the imine with a reducing agent (such as sodium borohydride, hydrogenation using palladium on carbon, or zinc in acetic acid). The formation of I is accomplished by a reaction of the product of the Boc-deprotection with VI in which Z is a halogen (or alternatives, such as a triflate, or mesylate) and a base (such as triethylamine), neat or in organic solvents (such as acetonitrile, or methylene chloride).

The steps in the reaction sequence depicted in Scheme 1 may be carried out in different order, for example in the order as shown in Scheme 2, with the reaction conditions and suitable reagents being substantially the same as those described above for Scheme 1.

Scheme 2

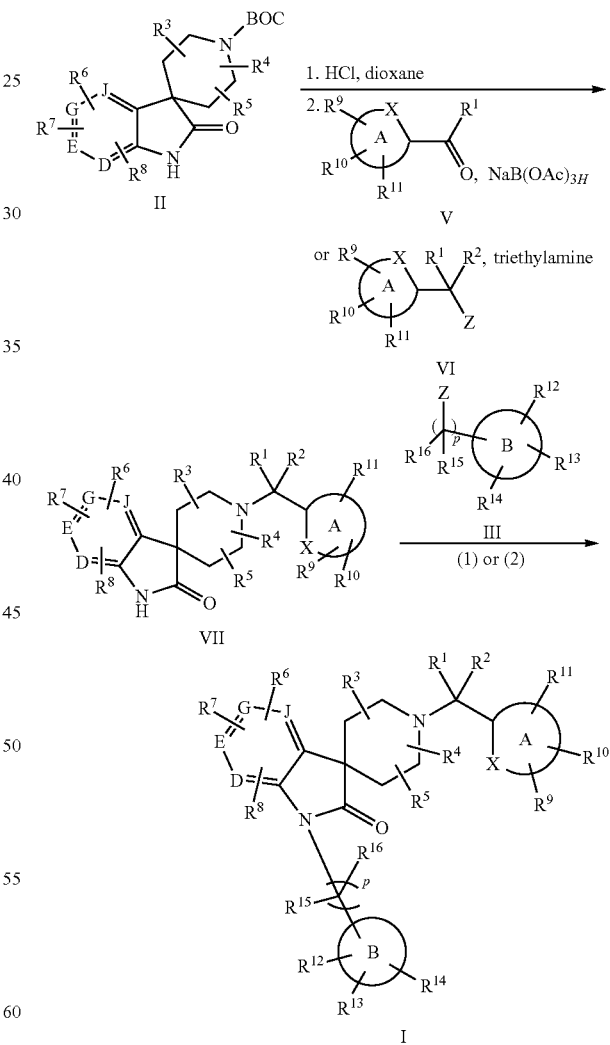

I

Z is halogen
(1) p is 0, and B is aryl or heteroaryl: CuI, K₂CO₃, MeCN, CH₃NH(CH₂)₂NHCH₃
(2) p is 0, and B is other than aryl or heteroaryl, or p is 1 and B is carbocycle or heterocycle: KF-alumina, MeCN

Preparation of Intermediate A

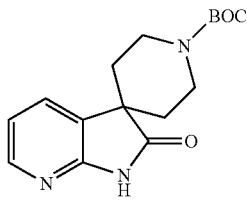 [SMILES: CC(C)(C)OC(=O)N1CCC2(CC1)C(=O)Nc1ncccc12]

A 12-L-three-neck flask equipped with an overhead stir, nitrogen inlet, a 2-L addition funnel, and an internal temperature probe was charged with 7-azaoxindole (72 g, 537 mmol) and anhydrous DME (2.5 L). The solution was cooled to −60° C. and LiHMDS (296 g, 1771 mmol) was added as solution in DME (1 L) via addition funnel over 30 minutes while the temperature was maintained at −60 to −54° C. The reaction was allowed to warm up −20° C. and stirred for 40 minutes. The mixture was cooled to −60° C. and a solution of N-BOC-bis(2-chloroethyl)amine (149 g, 617 mmol) in DME (0.5 L) was added within 2 minutes. The resulting reaction mixture was allowed to reach room temperature over 10 h, and stirred for 3 days. The reaction mixture was heated to 50° C. for 60 h, cooled to room temperature and poured onto 10 L of ice, combined with 4 L of AcOEt, separated, aqueous layer washed with additional 2 L of AcOEt, combined organic layers washed with brine and concentrated. Column chromatography afforded pure intermediate A as a solid.

The slurry was filtered and the cake washed with hexanes affording the title compound as a white solid.

Intermediate A corresponds to the spiro-aza-oxindole where the nitrogen in the aromatic ring six-member ring system corresponds to the "D" position of compound II as shown in general Schemes 1 and 2. To synthesis the other desired intermediates where the nitrogen is in the "E", "G", or "J" position, the appropriate aza-oxindole should be selected as starting material and the general procedure outlined for intermediate A should be followed.

Example 1

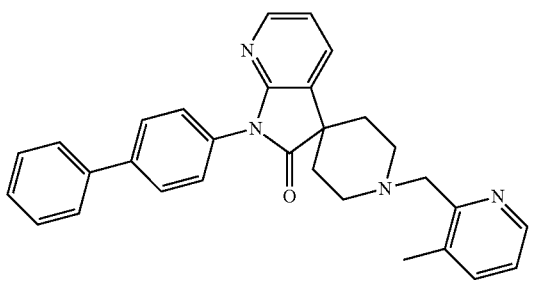 [SMILES: Cc1cccnc1CN1CCC2(CC1)C(=O)N(c1ccc(-c3ccccc3)cc1)c1ncccc12]

1'-biphenyl-4-yl-1-[3-methylpyridin-2-yl)methyl]spiro[piperidine-4,3'-pyrrolo[3,2-b]-pyridin]-2'(1'H-one Step A:

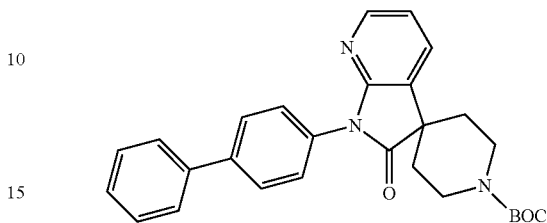

In an oven-dried flask, intermediate A (100 mg, 0.17 mmol) and 4-iodobiphenyl (0.21 mmol) were dissolved in acetonitrile (10 ml), and the mixture was degassed with stream of nitrogen through the solution at 40° C. for 20 minutes. Anhydrous potassium carbonate (0.5 mmol), copper (I) iodide (0.17 mmol), and N,N'-dimethylethylenediamine (0.17 mmol) were added sequentially and the resulting reaction mixture was heated for 15 h to 80° C. under nitrogen and then cooled to room temperature. The crude mixture was diluted with ethyl acetate and washed with 0.1M HCl solution, dried over sodium sulfate, filtered and concentrated. Further purification of the desired product was accomplished by column chromatography on silica gel: eluting with a gradient of ethyl acetate in hexanes: 0-40%/1.3 L. LCMS (Method B): 4.10 min, m/z (M-BocH)$^+$=356.1.

Step B:

4M HCl in dioxane (10 ml, 240 mmol) was added to the product of Step A (0.15 mmol) via syringe in one portion and the resulting mixture was stirred at ambient temperature for 1 h and concentrated LCMS (Method B) 2.5 min, m/z (MH)$^+$=356.

Step C:

To a solution of the product of Step B (0.15 mmol) in DCM (20 mL), 3-methylpyridine-2-carboxaldehyde (0.20 mmol) and sodium triacetoxyborohydride (0.60 mmol) were added sequentially and the resulting mixture was stirred at ambient temperature for 2 h. Methanol (20 mL) was added and the mixture was stirred at ambient temperature for 5 minutes and concentrated. The final purification was accomplished by preparative reverse phase HPLC (Method C) to give the title compound, isolated as a salt of trifluoroacetic acid; $^1$H NMR (400 MHz, CD$_3$OD) δ8.54 (d, J=4.6, 1H), 8.34 (dd, J=1.4, 4.6, 1H), 7.85 (d, J=8.2, 2H), 7.75 (d, J=7.8, 1H), 7.70 (d, J=7.5, 2H), 7.58 (d, J=8.2, 2H), 7.49 (t, J=7.5, 2H), 7.38 (m, 4H), 4.73 (s, 2H), 4.03 (m, 2H), 3.94 (m, 2H), 2.46 (m, 4H), 2.42 (s, 3H). LCMS (Method A): 1.84 min, m/z (MH)$^+$=462.1.

Examples 2-3

The following compounds, Examples 2 and 3, were prepared according to the general procedure described for Example 1, and isolated as salts of trifluoroacetic acid.

TABLE 1

| Ex. # | IUPAC name | Compound | ¹HNMR and/or LCMS |
|---|---|---|---|
| Ex. 2 | 1'-biphenyl-4-yl-1-[(3-methylpyridin-2-yl)methyl]spiro[piperidine-4,3'-pyrrolo[2,3-b]pyridin]-2'(1'H)-one | | 1H NMR (500 MHz, CD3OD): 2.38 (m, 2H), 2.41 (s, 3H), 2.56 (t, J = 5.6 Hz, 2H), 3.74 (m, 2H), 4.09 (t, J = 5.6 Hz, 2H), 4.73 (s, 2H), 7.23 (m, 1H), 7.41 (m, 2H), 7.48 (t, J = 4.2 Hz, 2H), 7.65 (d, J = 7.4 Hz, 2H), 7.70 (d, J = 7.4 Hz, 2H), 7.81 (d, J = 7.4 Hz, 1H), 7.82 (d, J = 7.4 Hz, 2H), 7.940 (d, J = 3.4 Hz, 1H), 8.21 (d, J = 2.4 Hz, 1H), 8.55 (d, J = 2.4 Hz, 1H); LCMS (method B) 3.04 min, m/z (MH)⁺ = 461.1. |
| Ex. 3 | 1'-biphenyl-4-yl-1-[(3-methylpyridin-2-yl)methyl]-2'-oxo-1',2'-dihydrospiro[piperidine-4,3'-pyrrolo[2,3-b]pyridine]-6'-carbonitrile | | ¹H NMR (400 MHz, CD₃OD) δ 8.51 (d, J = 4.3, 1H), 8.07 (d, J = 7.4, 1H), 7.78 (d, J = 8.5, 2H), 7.74 (d, J = 7.5, 1H), 7.68 (m, 3H), 7.62 (d, J = 8.5, 2H), 7.47 (t, J = 7.3, 2H), 7.37 (m, 2H), 4.68 (s, 2H), 3.98 (dt, J = 3.0, 12.6, 2H), 3.72 (d, J = 12.8, 2H), 2.58 (t, J = 14.9, 2H), 2.39 (s, 3H), 2.37 (d, J = 14.0, 2H). LCMS (Method A): 1.75 min, m/z (MH)⁺ = 486.2 |

Example 4

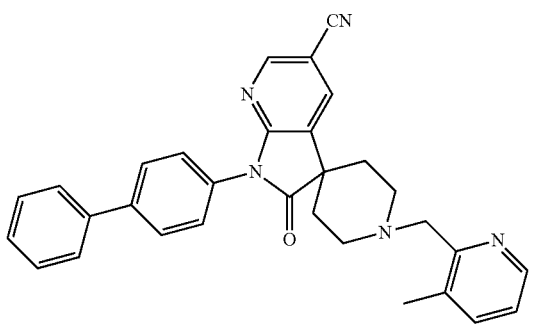 [SMILES: Cc1cccnc1CN1CCC2(CC1)C(=O)N(c1ccc(-c3ccccc3)cc1)c1ncc(C#N)cc12]

1'-biphenyl-4-yl-1-[(3-methylpyridin-2-1)methyl]-2'-oxo-1',2'-dihydrospiro[piperidine-4,3'-pyrrolo[2,3-b]pyridine]-5'-carbonitrile Step A:

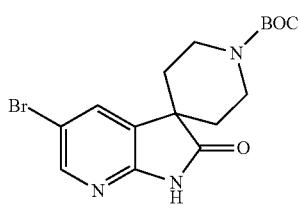 [SMILES: CC(C)(C)OC(=O)N1CCC2(CC1)C(=O)Nc1ncc(Br)cc12]

Intermediate A (1 g, 3.31 mmol) and N-bromosuccinimide (0.618 g, 3.47 mmol) were dissolved in DMF (20 ml) and stirred at ambient temperature for 20 h, and then combined with cold water (250 mL). A white precipitate was collected by filtration, the solids rinsed with additional 100 mL of water and dried in desiccator. Purification by a column chromatography using Biotage 40M, eluent: hexanes/ethyl acetate 0-60%/1.3 L provided the desired product, LCMS (Method B): 3.89 min, m/z (M-Boc)⁺=282.3.

Step B:

4M HCl in dioxane (60 ml, 240 mmol) was added to the bromiated intermediate A (2 g, 6.60 mmol) via syringe in one portion and the resulting mixture was stirred at ambient temperature for 1 h and concentrated. The white solids were dried in desiccator to provide the deprotected intermediate A. LCMS (Method B) 0.77 min, m/z (MH)⁺=282.2.

Step C:

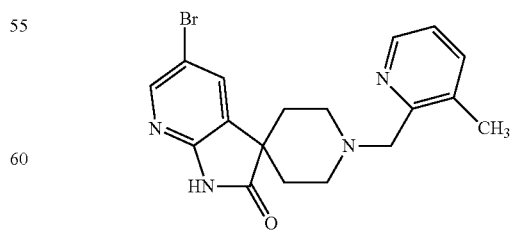

To a solution of the product of Step B (800 mg, 3.35 mmol) and 3-methylpyridine-2-carboxaldehyde (528 mg, 4.36 mmol) in DCM (15 ml), sodium triacetoxyborohydride was added and the resulting mixture was stirred at ambient temperature 1 h. Methanol (10 mL) was added and the mixture stirred for additional five minutes and concentrated. Further purification by preparative reverse phase HPLC (Method C) provided the desired product, isolated as a salt of trifluoroacetic acid; LCMS (Method B) 0.88 min, m/z (MH)$^+$=388.1.
Step D:

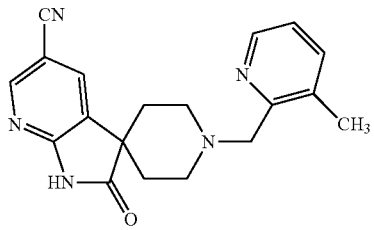 [SMILES: Cc1cccnc1CN1CCC2(CC1)C(=O)Nc1ncc(C#N)cc12]

The product of Step C (200 mg, 0.518 mmol), zinc cyanide (122 mg, 1.036 mmol), tris(dibenzylideneacetone)dipalladium (51.3 mg, 0.052 mmol) and 1,1'-bis(diphenylphosphino)-ferrocene (14.24 mg, 0.026 mmol) were combined in DMF (20 ml) and water (0.2 ml). The reaction mixture was degassed with a stream of nitrogen for 1 h and then heated under nitrogen atmosphere for 60 h at 115° C. and filtered. The solution of the crude reaction mixture was purified by preparative reverse phase HPLC (Method C), which provided the title compound, isolated as a salt of trifluoroacetic acid; LCMS (Method B): 3.17 min, m/z (MH)$^+$=485.4; $^1$H NMR (400 MHz, CD$_3$OD) δ8.61 (d, J=2.0, 1H), 8.55 (d, J=4.4, 1H), 8.30 (s, 1H), 7.81 (m, 2H), 7.77 (d, J=7.7, 1H), 7.69 (d, J=7.1, 2H), 7.49 (t, J=15.3, 2H), 7.40 (t, J=7.1, 2H), 4.74 (s, 2H), 4.03 (t, J=11.6, 2H), 3.74 (m, 2H), 2.55 (m, 2H), 2.45 (m, 2H), 2.41 (s, 3H). LCMS (Method A): 1.74 min, m/z (MH)$^+$= 486.0.

Example 5

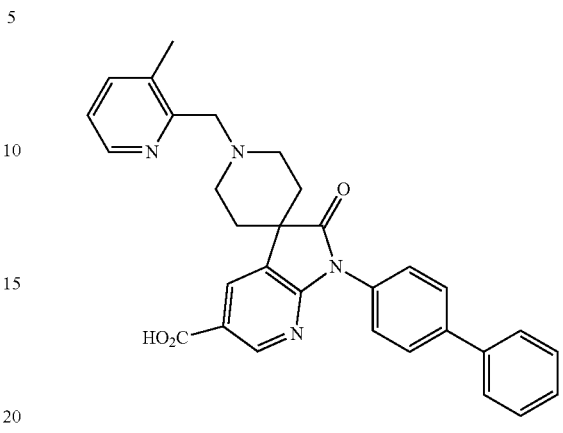

1'-biphenyl-4-yl-1-[(3-methylpyridin-2-yl)methyl]-2'-oxo-1',2'-dihydrospiro[piperidine-4,3'-pyrrolo[2,3-b]pyridine]-5'-carboxylic acid The title compound of Example 4, 1'-biphenyl-4-yl-1-[(3-methylpyridin-2-yl)methyl]-2'-oxo-1',2'-dihydrospiro[piperidine-4,3'-pyrrolo[2,3-b]pyridine]-5'-carbonitrile, (1 mmol) was combined with anhydrous ethanol (10 mL) and neat sulfuric acid (1 mL) was added drop wise to the solution over 2 minutes. The resulting mixture is heated in a sealed tube to 100° C., allowed to cool to room temperature and combined with ice water. The resulting mixture was extracted with methylene chloride, dried and concentrated. The crude oil is combined with THF (10 mL), water (5 mL) and lithium hydroxide (20 mmol) and heated to 50° C. for 5 h, acidified with 1 m HCl, concentrated and purified by preparative reverse phase HPLC (method C), which provided the title compound, isolated as a salt of trifluoroacetic acid.

The following compounds were prepared according to the general procedure described for Example 5, and isolated as salts of trifluoroacetic acid.

TABLE 2

| Ex. # | IUPAC name | Compound | $^1$H NMR and/or LCMS |
|---|---|---|---|
| Ex. 6 | 1'-biphenyl-4-yl-1-[(3-methylpyridin-2-yl)methyl]-2'-oxo-1',2'-dihydrospiro[piperidine-4,3'-pyrrolo[2,3-b]pyridine]-6'-carboxylic acid | (structure) | $^1$H NMR (400 MHz, CD$_3$OD) δ 8.54 (d, J = 4.3, 1H), 8.07 (m, 1H), 8.01 (d, J = 7.3, 1H), 7.80 (d, J = 8.4, 2H), 7.75 (d, J = 7.3, 1H), 7.69 (t, J = 5.9, 4H), 7.48 (t, J = 7.5, 2H), 7.38 (m, 2H), 4.72 (s, 2H), 4.05 (t, J = 10.1, 2H), 3.75 (d, J = 12.8, 2H), 2.58 (t, J = 11.4, 2H), 2.40 (s, 3H). LCMS (Method A): 1.49 min, m/z (MH)$^+$ = 505.1 |

TABLE 2-continued

| Ex. # | IUPAC name | Compound | ¹H NMR and/or LCMS |
|---|---|---|---|
| Ex. 7 | (1'-biphenyl-4-yl-5'-bromo-2'-oxo-1',2'-dihydro-1H-spiro[piperidine-4,3'-pyrrolo[2,3-b]pyridin]-1-yl)acetic acid | | ¹H NMR (400 MHz, CD3OD) δ 8.28 (d, J = 1.8, 1H), 8.10 (s, 1H), 7.77 (d, J = 8.2, 2H), 7.67 (d, J = 7.5, 2H), 7.60 (d, J = 8.5, 2H), 7.47 (t, J = 7.6, 2H), 7.37 (t, J = 7.3, 1H), 4.25 (s, 2H), 3.95 (m, 2H), 3.69 (d, J = 11.7, 2H), 2.38 (m, 4H). LCMS (Method A): 1.67 min, m/z (MH)+ = 493.6 |
| Ex. 8 | (1'-biphenyl-4-yl-5'-cyano-2'-oxo-1',2'-dihydro-1H-spiro[piperidine-4,3'-pyrrolo[2,3-b]pyridin]-1-yl)acetic acid | | ¹H NMR (400 MHz, CD3OD) δ 8.59 (d, J = 1.8, 1H), 8.26 (s, 1H), 7.80 (d, J = 8.4, 2H), 7.69 (d, J = 7.3, 2H), 7.61 (d, J = 6.6, 2H), 7.48 (t, J = 7.5, 2H), 7.39 (t, J = 7.4, 1H), 4.22 (s, 2H), 3.94 (m, 2H), 3.71 (m, 2H), 2.66 (s, 2H), 2.42 (m, 4H). LCMS (Method A): 1.50 min, m/z (MH)+ = 439.0 |
| Ex. 9 | (1'-biphenyl-4-yl-2'-oxo-1',2'-dihydro-1H-spiro[piperidine-4,3'-pyrrolo[2,3-b]pyridin]-1-yl)acetic acid | | ¹H NMR (500 MHz, CD3OD): 2.34 (m, 2H), 2.47 (m, 2H), 3.70 (m, 2H), 3.96 (m, 2H), 4.24 (s, 2H), 7.19-7.91 (m, 11H), 8.16 (d, 1H, J = 4.6 Hz); LCMS (Method A): 1.50 min, m/z (MH)⁺ = 4143.0 |
| Ex. 10 | 1'-biphenyl-4-yl-1-(carboxymethyl)-2'-oxo-1',2'-dihydrospiro[piperidine-4,3'-pyrrolo[2,3-b]pyridine]-5'-carboxylic acid | | LCMS (Method A): 1.44 min, m/z (MH)⁺ = 458.0 |

Definition of Methods A-C for HPLC Analysis and Purification:

Method A:

Conditions for LCMS: Mass Spectrometer: Micromass ZQ single quadrupole, Electrospray Positive Ionization, Full Scan mode (150-750 amu in 0.5 s); HPLC: Agilent 1100, Binary Pump; DAD UV detector: Hardware/software Waters/Micromass MassLynx 4.0; Column: Waters Xterra, 3.0 mm Width, 50 mm Length, 3.5 micron packing material; Runtime: 5.5 min; Flow Rate: 1.0 ml/min.; Mobile Phase A=Water+0.05% TFA, B=Acetonitrile+0.05% TFA; Gradient: Time/% A/% B: 0.00/90/10, 3.25/2/98, 3.75/2/98, 4.00/90/10.

Method B:

Conditions for LCMS: Mass Spectrometer: Micromass ZQ single quadrupole, Electrospray Positive Ionization, Full Scan mode (150-750 amu in 0.5 s); HPLC: Agilent 1100, Binary Pump; DAD UV detector: Hardware/software Waters/Micromass MassLynx 4.0; Column: Waters Xterra, 3.0 mm Width, 50 mm Length, 3.5 micron packing material; Runtime: 5.5 min; Flow Rate: 1.0 ml/min.; Mobile Phase A=Water+0.05% TFA, B=Acetonitrile+0.05% TFA; Gradient: Time/% A/% B: 0.00/90/10, 3.75/2/98, 4.75/2/98, 4.76/90/10, 5.5/90/10.

Method C:

Preparative reverse phase liquid chromatography (RPHPLC) was performed using Waters MS Directed Purification System consisting of 2525 Binary Gradient Pump, 2767 Injector/Collector and 2996 PDA UV detector, mobile phase: gradient of water and acetonitrile (each cont. 0.1% TFA), column: Waters Xterra (50×3 mm, 3.5 micron packing material).

Biological Assays

The exemplified compounds, Examples 1 through 10 of the present invention, have been found to inhibit the interaction between PHD2 and a HIF peptide and exhibit $IC_{50}$ values ranging between 0.1 nanomolar to 10 micromolar. Non-limiting examples of assays that may be useful to detect favorable activity are disclosed in the following publications: Oehme, F., et al., *Anal. Biochem.* 330:74-80 (2004); Hirsilä, M, et al., *J. Bio. Chem.* 278 (33): 30772-30780 (2005); Hyunju, C., et al., *Biochem. Biophys. Res. Comm.* 330 (2005) 275-280; and Hewitson, K. S., et al., *Methods in Enzymology*, (Oxygen Biology and Hypoxia); Elsevier Publisher (2007), pg. 25-42 (ISSN: 0076-6879).

The biological activity of the present compounds may be evaluated using assays described herein below.

Assay for HIF-PHD2 Catalytic Activity

To each well of a 96-well plate was added 1 µL of test compound in DMSO and 20 µl of assay buffer (50 mM Tris pH 7.4/0.01% Tween-20/0.1 mg/ml bovine serum albumin/10 µM ferrous sulfate/1 mM sodium ascorbate/20 µg/ml catalase) containing 0.15 µg/ml FLAG-tagged full length PHD2 expressed in and purified from baculovirus-infected Sf9 cells. After a 30 min preincubation at room temperature, the enzymatic reactions were initiated by the addition of 4 µL of substrates (final concentrations of 0.2 µM 2-oxoglutarate and 0.5 µM HIF-1α peptide biotinyl-DLDLEMLAPYIPMD-DDFQL). After 2 hr at room temperature, the reactions were terminated and signals were developed by the addition of a 25 µL quench/detection mix to a final concentration of 1 mM ortho-phenanthroline, 0.1 mM EDTA, 0.5 nM anti-$(His)_6$ LANCE reagent (Perkin-Elmer Life Sciences), 100 nM AF647-labeled streptavidin (Invitrogen), and 2 µg/ml $(His)_6$-VHL complex (S. Tan (2001) Protein Expr. Purif. 21, 224-234). The ratio of time resolved fluorescence signals at 665 and 620 nm was determined, and percent inhibition was calculated relative to an uninhibited control sample run in parallel.

Inhibition of the catalytic activity of HIF-PHD 1 and HIF-PHD3 can be determined similarly.

Table 3 lists the PHD2 binding activity expressed as $IC_{50}$ (nM), for the compounds of the present invention disclosed in Example 1 through Example 192.

TABLE 3

PHD2 binding activity for the examples listed expressed as $IC_{50}$ (nM):
+ = ≦5
++ = >5 to ≦10
+++ = >10 nM to ≦50

| Example | | PHD2 Activity |
|---|---|---|
| 1 | 1'-biphenyl-4-yl-1-[(3-methylpyridin-2-yl)methyl]spiro[piperidine-4,3'-pyrrolo[3,2-b]pyridin]-2'(1'H)-one | + |
| 2 | 1'-biphenyl-4-yl-1-[(3-methylpyridin-2-yl)methyl]spiro[piperidine-4,3'-pyrrolo[2,3-b]pyridin]-2'(1'H)-one | + |
| 3 | 1'-biphenyl-4-yl-1-[(3-methylpyridin-2-yl)methyl]-2'-oxo-1',2'-dihydrospiro[piperidine-4,3'-pyrrolo[2,3-b]pyridine]-6'-carbonitrile | + |
| 4 | 1'-biphenyl-4-yl-1-[(3-methylpyridin-2-yl)methyl]-2'-oxo-1',2'-dihydrospiro[piperidine-4,3'-pyrrolo[2,3-b]pyridine]-5'-carbonitrile | ++ |
| 5 | 1'-biphenyl-4-yl-1-[(3-methylpyridin-2-yl)methyl]-2'-oxo-1',2'-dihydrospiro[piperidine-4,3'-pyrrolo[2,3-b]pyridine]-5'-carboxylic acid | + |
| 6 | 1'-biphenyl-4-yl-1-[(3-methylpyridin-2-yl)methyl]-2'-oxo-1',2'-dihydrospiro[piperidine-4,3'-pyrrolo[2,3-b]pyridine]-6'-carboxylic acid | + |
| 7 | (1'-biphenyl-4-yl-5'-bromo-2'-oxo-1',2'-dihydro-1H-spiro[piperidine-4,3'-pyrrolo[2,3-b]pyridin]-1-yl)acetic acid | +++ |
| 8 | (1'-biphenyl-4-yl-5'-cyano-2'-oxo-1',2'-dihydro-1H-spiro[piperidine-4,3'-pyrrolo[2,3-b]pyridin]-1-yl)acetic acid | +++ |
| 9 | (1'-biphenyl-4-yl-1'-oxo-1',2'-dihydro-1H-spiro[piperidine-4,3'-pyrrolo[2,3-b]pyridin]-1-yl)acetic acid | +++ |
| 10 | 1'-biphenyl-4-yl-1-(carboxymethyl)-2'-oxo-1',2'-dihydrospiro[piperidine-4,3'-pyrrolo[2,3-b]pyridine]-5'-carboxylic acid | ++ |

What is claimed is:

1. A compound of formula I and pharmaceutically acceptable salts and solvates thereof:

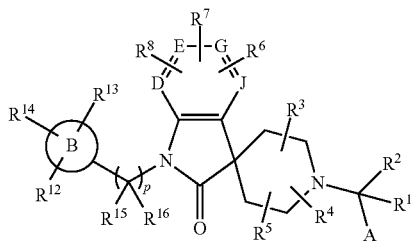

wherein

A is hydrogen, carboxyl, or A is a heterocyle having at least one heteroatom, X, of formula

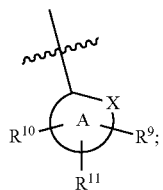

X is selected from N, O and S;

B is a carbocycle or a heterocycle;

at least one of D, E, G, and J, is nitrogen and the rest are carbon;

p is 0 or 1;

$R^1$, $R^2$, $R^{15}$ and $R^{16}$ are independently selected from i) hydrogen; ii) $C_1$-$C_4$ alkyl, optionally substituted with a hydroxy, —SH, —$NH_2$ or —$CO_2H$; iii) trifluoromethyl; iv) 2,2,2-trifluoroethyl; and v) —$CO_2H$;

$R^3$, $R^4$ and $R^5$ are independently selected from hydrogen, F, OH, $C_1$-$C_4$ alkyl, $C_1$-$C_4$ haloalkyl, —$OC_1$-$C_4$ alkyl,)-, ($C_0$-$C_6$ alkyl)$_2$NC(O)—, —($C_0$-$C_6$ alkyl)C(O)NH($C_0$-$C_6$ alkyl), —($C_0$-$C_6$ alkyl)C(O)O($C_0$-$C_6$ alkyl), —($C_0$-$C_6$ alkyl)aryl, —($C_0$-$C_6$ alkyl)C(O)aryl, —($C_0$-$C_6$ alkyl)C(O)heteroaryl, and —($C_0$-$C_6$ alkyl)heteroaryl, where aryl, heteroaryl and are each optionally substituted with one to three groups independently selected from halo, $C_1$-$C_6$ alkyl, —O($C_1$-$C_6$ alkyl) and cyano;

$R^3$ and $R^4$ attached to the same carbon atom together form an oxo group or complete a $C_3$-$C_6$ cycloalkyl ring, or $R^3$ and $R^4$ attached to adjacent carbon atoms together complete a $C_3$-$C_6$ cycloalkyl ring, or $R^3$ and $R^4$ attached to nonadjacent carbon atoms together represent $C_1$-$C_2$ alkylene;

$R^6$, $R^7$, $R^8$, $R^9$, $R^{10}$, $R^{11}$, $R^{12}$, $R^{13}$ and $R^{14}$ are independently selected from hydrogen, halo, $C_1$-$C_6$ alkyl optionally substituted with one to five fluorine, $NH_2$, $N(C_1$-$C_6$ alkyl)$_2$, $NO_2$, CN, $N_3$, —OH, —O($C_1$-$C_6$ alkyl) optionally substituted with one to five fluorine, $C_3$-$C_{10}$ cycloalkyl, $C_2$-$C_6$ alkenyl, $C_2$-$C_6$ alkynyl, —O-aryl, aryl-S(O)$_{0-2}$—, ($C_0$-$C_6$ alkyl)S(O)$_{0-2}$($C_0$-$C_6$ alkylene)-, ($C_0$-$C_6$ alkyl)C(O)NH—, $H_2$N—C(NH)—, ($C_0$-$C_6$ alkyl)C(O)—, ($C_0$-$C_6$ alkyl)OC(O)($C_0$-$C_6$ alkylene)-, ($C_0$-$C_6$alkyl)O($C_1$-$C_6$ alkylene)-, ($C_0$-$C_6$ alkyl)C(O)$_{1-2}$ ($C_0$-$C_6$ alkylene)-, ($C_0$-$C_6$ alkyl)$_2$NC(O)—, ($C_0$-$C_6$ alkyl)OC(O)NH—, aryl, aralkyl, heteroaryl, and heteroaralkyl, where aryl, aralkyl, heteroaryl and heteroaralkyl are each optionally substituted with one to three groups, $R^{17}$, $R^{18}$ and $R^{19}$, independently selected from halo, $C_1$-$C_6$ alkyl, —O($C_1$-$C_6$ alkyl) and cyano;

wherein any two of $R^{12}$, $R^{13}$, $R^{14}$, $R^{17}$, $R^{18}$ and $R^{19}$ together with the atoms of the ring system, B, form a 5 to 8-membered ring.

2. A compound of claim 1 wherein A is a group of formula

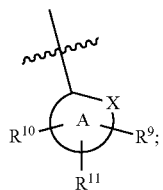

wherein A is a 5-membered heteroaromatic ring in which X is nitrogen, and the ring optionally having one to three additional heteroatoms selected from N, O and S.

3. A compound of claim 1 wherein A is a group of formula

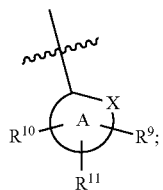

wherein A is a 6-membered heteroaromatic ring in which X is nitrogen, and the ring optionally having one additional nitrogen atom.

4. A compound of claim 1 wherein A is selected from hydrogen carboxyl, or the group

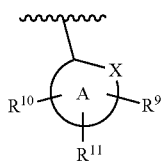

selected from 1-methyl-2-imidazolyl, 3-methyl-2-pyridyl, 3-cyclopropyl-2-pyridyl, 1-(2-pyridylmethyl)-2-pyrrolyl, 1-(methoxycarbonylmethyl)-2-imidazolyl, 1-(carboxymethyl)-2-imidazolyl, 3,5-dimethyl-2-pyridyl, 1-benzyl-2-imidazolyl, 3-trifluoromethyl-2-pyridyl, 3-(methoxy carbonyl)methyl-2-pyridyl, 1-(aminocarbonyl methyl)-2-imidazolyl, 1-(aminocarbonyl methyl)-2-pyridinyl, 3-carboxy-2-pyridyl, 1-(aminocarbonyl)-2-pyridinyl, 1-(aminocarbonyl)-2-imidazolyl imidazolyl, carboxyl, and 1-(carboxyethyl)-1-imidazolyl.

5. A compound of claim 1 wherein B is aryl or a 7- to 12-membered bicyclic heterocycle.

6. A compound of claim 1 wherein B is an 8- to 12-membered bicyclic heteroaromatic ring system.

7. A compound of claim 1 wherein B is selected from the group consisting of phenyl, 4-biphenyl, 3-biphenyl, 1-naphthyl, 2-naphthyl, 3-quinolinyl, 5-quinolinyl, 6-quinolinyl, 7-quinolinyl, 6-isoquinolinyl, 7-isoquinolinyl, 7-quinoxalinyl, 6-quinazolinyl, 7-cinnolinyl, 5-indolyl, pyrazolo[3,4-b]pyrid-5-yl, 1,4-benzoxazinyl, 1,3-benzoxazolinyl, 4-(1-pyrrolyl)phenyl, 4-(3-pyridyl)phenyl, 6-(1-pyrrolyl)-3-pyridyl, pyridyl, chromonyl, thiazolyl, thienyl, 4-(2-thienyl)-phenyl, fluorenyl, (9-oxo)-2-fluorenyl, 2-phenyl)-4-(1,3-thiazolyl), and 2-phenyl-5-(1,3-thiazolyl).

8. A compound of claim 1 wherein D is nitrogen.
9. A compound of claim 1 wherein E is nitrogen.
10. A compound of claim 1 wherein G is nitrogen.
11. A compound of claim 1 wherein J is nitrogen.
12. A pharmaceutical composition comprising a compound of claim 1 and pharmaceutically acceptable carrier.

13. A method of enhancing endogenous production of erythropoietin in a mammal which comprises administering to the mammal an amount of a compound of claim 1, or a pharmaceutically acceptable salt or solvate thereof, that is effective for enhancing endogenous production of erythropoietin.

14. A method for the treatment of anemia in a mammal which comprises administering to the mammal an effective amount of a compound of claim 1, or a pharmaceutically acceptable salt or solvate thereof.

15. A compound according to claim 1 selected from the group consisting of:
   1'-biphenyl-4-yl-1-[(3-methylpyridin-2-yl)methyl]spiro[piperidine-4,3'-pyrrolo[3,2-b]pyridin]-2'(1'H)-one;
   1'-biphenyl-4-yl-1-[(3-methylpyridin-2-yl)methyl]spiro[piperidine-4,3'-pyrrolo[2,3-b]pyridin]-2'(1'H)-one;
   1'-biphenyl-4-yl-1-[(3-methylpyridin-2-yl)methyl]-2'-oxo-1',2'-dihydrospiro[piperidine-4,3'-pyrrolo[2,3-b]pyridine]-6'-carbonitrile;
   1'-biphenyl-4-yl-1-[(3-methylpyridin-2-yl)methyl]-2'-oxo-1',2'-dihydrospiro[piperidine-4,3'-pyrrolo[2,3-b]pyridine]-5'-carbonitrile
   1'-biphenyl-4-yl-1-[(3-methylpyridin-2-yl)methyl]-2'-oxo-1',2'-dihydrospiro[piperidine-4,3'-pyrrolo[2,3-b]pyridine]-5'-carboxylic acid;
   1'-biphenyl-4-yl-1-[(3-methylpyridin-2-yl)methyl]-2'-oxo-1',2'-dihydrospiro[piperidine-4,3'-pyrrolo[2,3-b]pyridine]-6'-carboxylic acid;
   (1'-biphenyl-4-yl-5'-bromo-2'-oxo-1',2'-dihydro-1H-spiro[piperidine-4,3'-pyrrolo[2,3-b]pyridin]-1-yl)acetic acid;
   (1'-biphenyl-4-yl-5'-cyano-2'-oxo-1',2'-dihydro-1H-spiro[piperidine-4,3'-pyrrolo[2,3-b]pyridin]-1-yl)acetic acid;
   (1'-biphenyl-4-yl-2'-oxo-1',2'-dihydro-1H-spiro[piperidine-4,3'-pyrrolo[2,3-b]pyridin]-1-yl)acetic acid; and
   1'-biphenyl-4-yl-1-(carboxymethyl)-2'-oxo-1',2'-dihydrospiro[piperidine-4,3'-pyrrolo[2,3-b]pyridine]-5'-carboxylic acid; and pharmaceutically acceptable salts and solvates thereof.

* * * * *